United States Patent [19]

Sheriff et al.

[11] Patent Number: 4,728,812

[45] Date of Patent: Mar. 1, 1988

[54] ORAL MACHINE CONTROLLER

[76] Inventors: Paul S. Sheriff, 1003 Hunakai St., Honolulu, Hi. 96816; Randal J. York, 1760 Jonquil La., Plymouth, Minn. 55441

[21] Appl. No.: 882,366

[22] Filed: Jul. 7, 1986

[51] Int. Cl.⁴ ............................................. H01H 35/00
[52] U.S. Cl. .................................. 307/134; 200/85 R; 200/DIG. 2; 112/277; 128/777; 128/787
[58] Field of Search ............ 307/134; 200/52 R, 85 R, 200/61.58, 61.48, 86 R, 165, DIG. 2, 81 R; 128/359, 360, 78, 777, 1 R; 340/407, 539; 181/21; 414/9; 112/271, 277, 287, 217.3, 217.4; 116/205; 188/162, 2 F; 180/167, 907

[56] References Cited

U.S. PATENT DOCUMENTS

| | | | |
|---|---|---|---|
| 1,043,755 | 11/1912 | Christianson | 200/DIG. 2 |
| 3,207,161 | 9/1965 | Dietz | 128/787 |
| 3,459,145 | 8/1969 | Ramsey et al. | |
| 3,795,281 | 3/1974 | Cloran | 200/DIG. 2 |
| 3,935,405 | 1/1986 | Auer | |
| 3,983,865 | 10/1976 | Shepard | 128/777 |
| 4,045,630 | 8/1977 | McCarthy et al. | |
| 4,078,627 | 3/1978 | Brown et al. | |
| 4,086,458 | 4/1978 | Dickey | 200/85 R |
| 4,104,876 | 8/1978 | Landau, Jr. et al. | |
| 4,117,863 | 10/1978 | Gabus | 116/205 X |
| 4,232,687 | 11/1980 | Anderson-Shanklin | 128/777 |
| 4,260,035 | 4/1981 | Loveless et al. | |
| 4,284,018 | 8/1981 | Szostak | 112/217.4 |
| 4,359,953 | 11/1982 | Martell et al. | |
| 4,390,028 | 6/1983 | Okano et al. | 128/777 |
| 4,402,326 | 9/1983 | Okano et al. | 128/777 X |
| 4,488,873 | 12/1984 | Bloomfield et al. | 128/777 X |
| 4,521,186 | 6/1985 | Wodlinger et al. | 128/777 X |
| 4,583,474 | 4/1986 | Tysinger | 112/277 X |

Primary Examiner—William M. Shoop, Jr.
Assistant Examiner—Paul Ip
Attorney, Agent, or Firm—Schroeder & Siegfried

[57] ABSTRACT

The oral machine controller is an apparatus for controlling operations of a machine by jaw and tongue movement of an operator. Upper and lower dentition grips include thermoplastic members which are conformed to tooth shape to cling thereto. A lightweight control unit in a housing includes a straight potentiometer which generates a controllably variable voltage signal to control a speed or intensity function of the machine. One dentition grip is attached to the control unit housing by a first control arm and the other to a second control arm which is attached to a moveable contact on the potentiometer for changing its position and controlling the speed or intensity function of the machine. A tongue-actuated microswitch is provided for additional control of machine functions.

19 Claims, 13 Drawing Figures

U.S. Patent    Mar. 1, 1988    Sheet 1 of 4    4,728,812
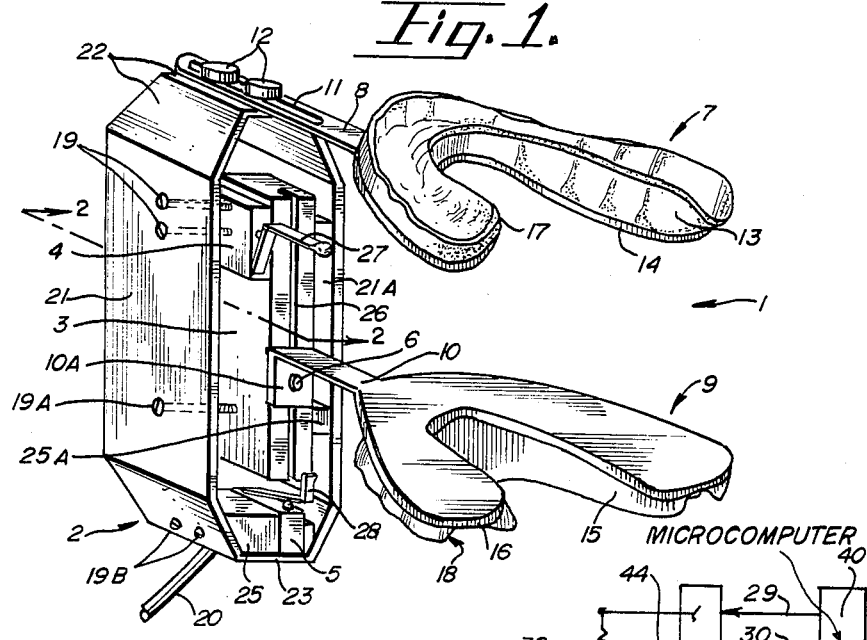
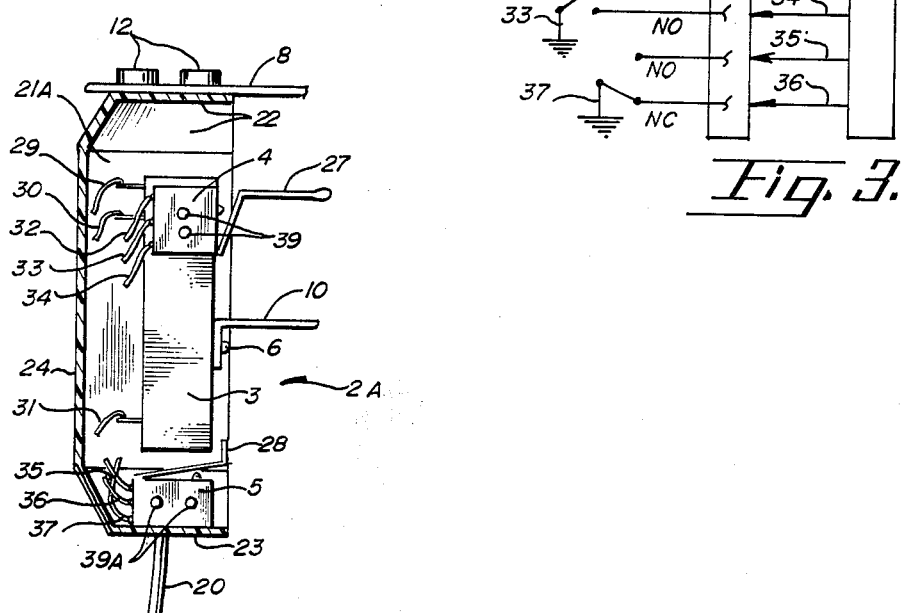

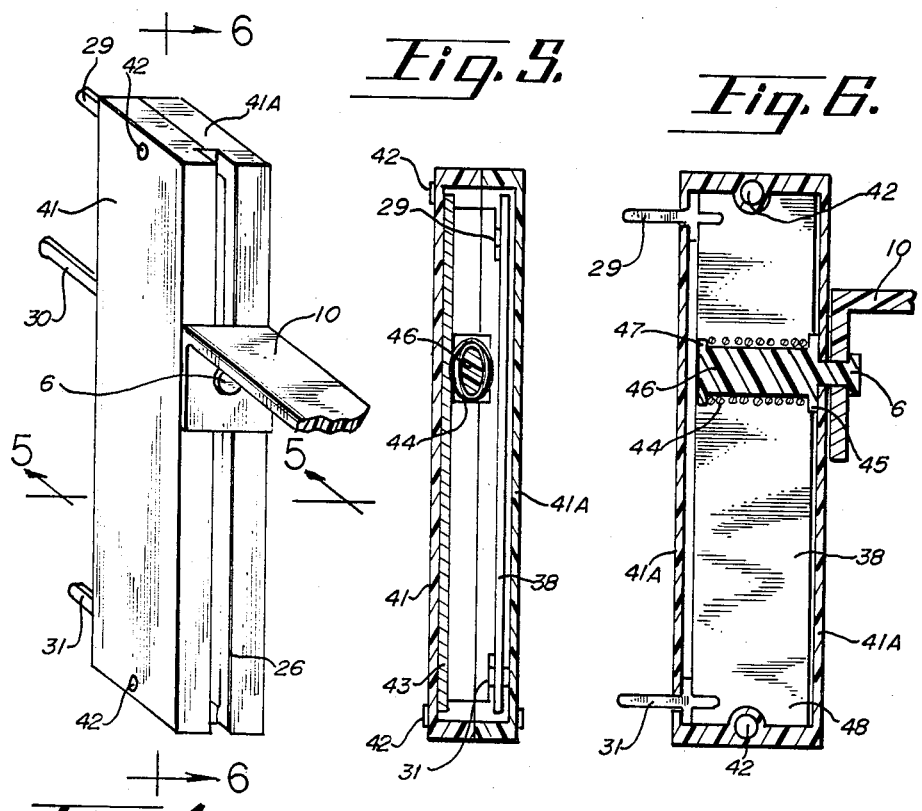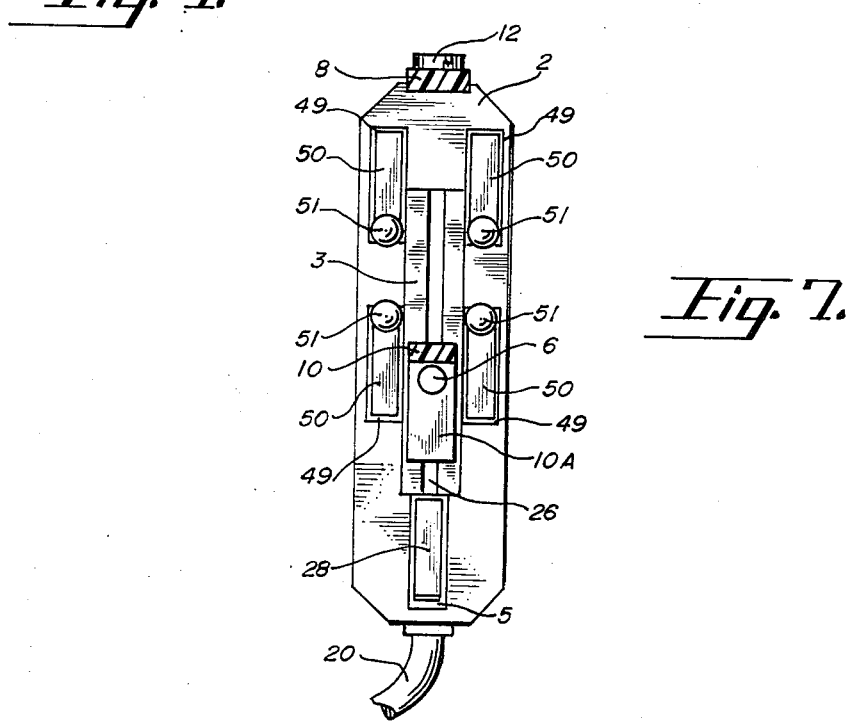

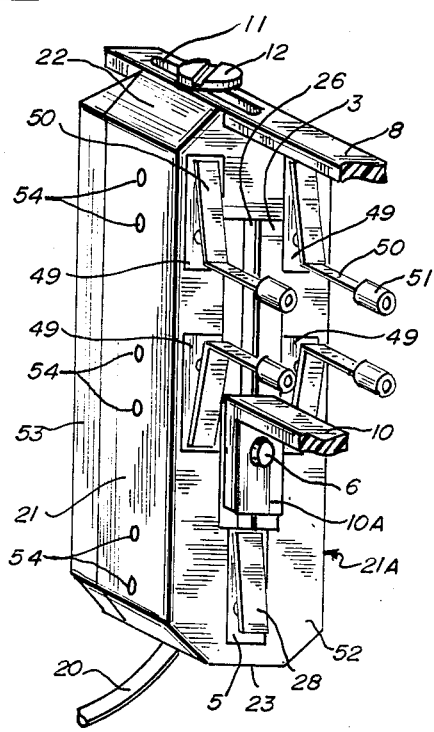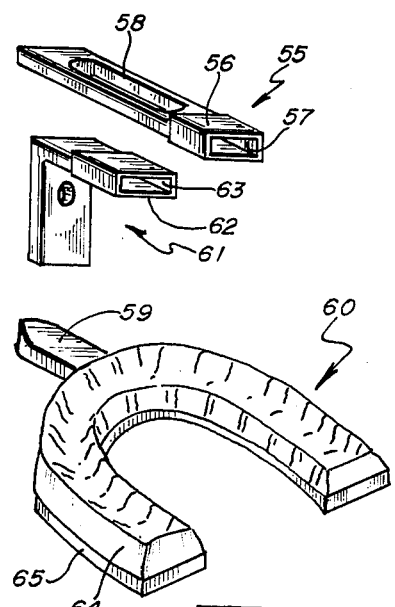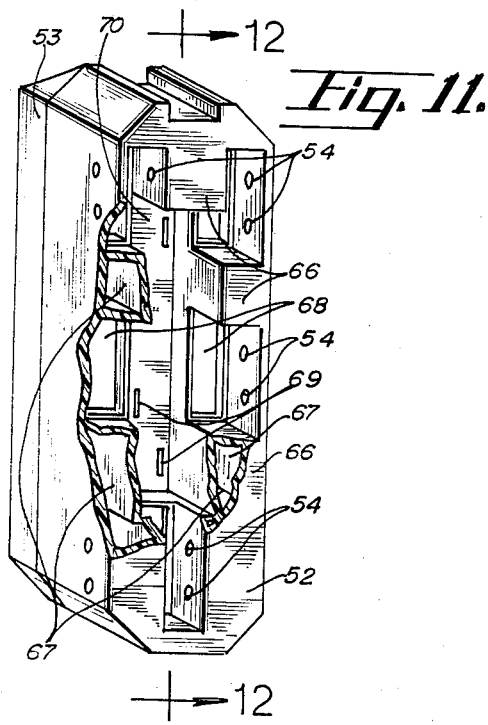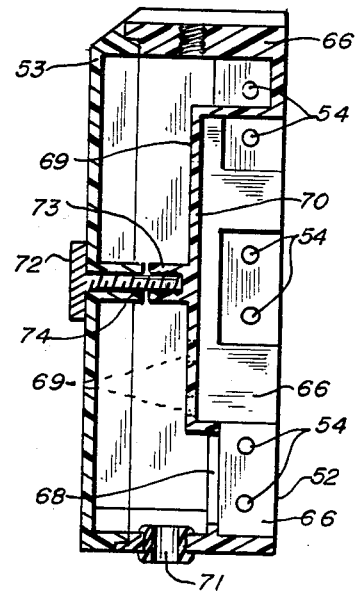

ORAL MACHINE CONTROLLER

BACKGROUND OF THE INVENTION

This invention relates to apparatus for converting oral motions of a human operator into electrical or electronic signals for controlling machines. More specifically, this is an apparatus with which a paraplegic, amputee or other disabled person, or a non-disabled person, may control a machine such as a programmable sewing machine, wheelchair, or an industrial or other mechanical device by oral movement such as by the jaw and tongue.

Many machines are designed to be operated by a combination of hand and foot motions. For example, automatic and semi-automatic sewing machines require not only hand dexterity, but typically also require foot or leg dexterity for operation of a foot treadle or a knee shift device. Such machines cannot be operated by persons who have lost the use of lower limbs by paralysis or amputation.

Likewise, wheelchairs used by such persons require control of speed, steering, braking and at least one ON-OFF function. Quadriplegics having neither arm nor leg functions must operate all control functions of the wheelchair by means other than hands or feet. Control units exist which are attached to the wheelchair and use chin motion and/or head motion for wheelchair control. However, such units do not permit independent head movement of the operator. The continuous and substantially immobile contact of chin with the control unit while operating the wheelchair causes discomfort to the operator.

SUMMARY OF THE INVENTION

The present invention is an apparatus for controlling mechanical and/or electrical operations of a machine, and is actuated by oral means such as jaw and tongue movement of the operator. Upper and lower dentition grips include thermoplastic members which may be conformed in vivo at a somewhat elevated temperature to removeably embrace and cling to the upper and lower teeth, respectively, of the operator.

A control unit is provided which is rigidly or semi-rigidly attached to one of the dentition grips and is supported thereby. A variable electrical means such as a potentiometer is mounted in the control unit housing and includes means such as an electrical resistance member with electrical terminals attached at each end for supplying electrical potential difference thereto. A moveable control or contact member is in contact with the resistance member and establishes an electrical control circuit. This moveable contact member is attached to the other dentition grip and is moved thereby. Movement such as linear movement of the contact member along the resistance member varies the resistance (thus varying the potential difference of an electrical control circuit) and provides a controllably variable voltage potential suitably conducted via conductor means to the machine for controlling various operation.

Optionally, a microswitch may be mounted in the housing to be contacted and actuated by the moveable contact member to turn the function controlled by the potentiometer (or equivalent) on and/or off.

One or more microswitches may be mounted on either side of the potentiometer, with detent members projecting into the vicinity of the operator's tongue. These microswitches are for tongue operation and useful to control the transmission of electronic signals over conductor means such as wires to the machine for controlling any function amenable to such control.

The control unit of this invention is lightweight and permits freedom of head movement. Many other features and benefits of this invention will become evident in this description.

BRIEF DESCRIPTION OF THE DRAWINGS

The present invention will now be described in more detail by way of example with reference to the accompanying drawings, wherein:

FIG. 1 is a perspective front view of the invention.

FIG. 2 is a side elevation view taken along line 2—2 of FIG. 1.

FIG. 3 is a schematic representation of the control system as adapted to a programmable sewing machine, illustrating the input and output signals thereof.

FIG. 4 is an enlarged perspective view of the potentiometer used in this invention.

FIG. 5 is a cross-sectional front view of the potentiometer taken along line 5—5 of FIG. 4.

FIG. 6 is a cross-sectional side view of the potentiometer taken along line 6—6 of FIG. 4.

FIGS. 7 and 8 are a front view and a perspective view, respectively, of an alternate embodiment of the control unit of this invention.

FIG. 9 is a perspective view of alternate forms of the first and second control arms.

FIG. 10 is a perspective view of an alternate form of dentition grip.

FIG. 11 is a perspective cut-away view of the control unit housing shown in FIG. 8.

FIG. 12 is a cross-sectional side view of the control unit housing as taken along line 12—12 of FIG. 11.

DESCRIPTION OF THE PREFERRED EMBODIMENTS

Figure 13:
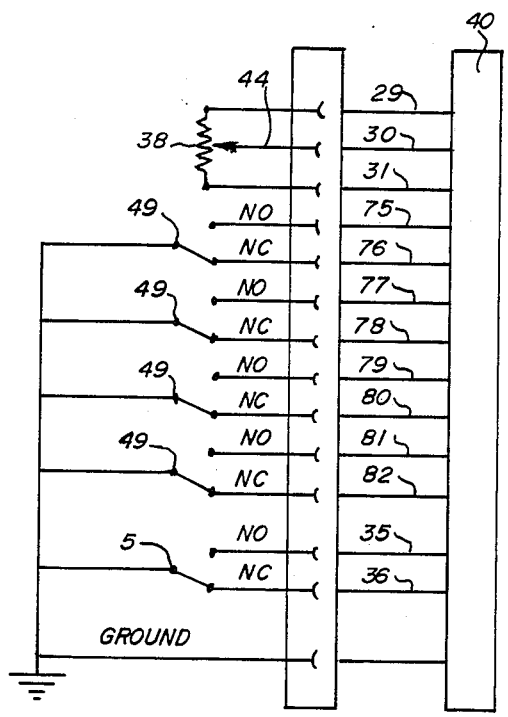
FIG. 13 is a schematic representation of the control system of FIGS. 7 and 8, illustrating input and output signals thereof.

As shown in FIG. 1, the oral machine controller 1 of this invention is comprised of several elements. Housing 2 encloses and provides mounting for electrical control members 3, 4, and 5. The housing and control members 3, 4, and 5 together comprise a control unit 2A. While the housing 2 may have any shape, it is preferably of minimum size and weight for comfortable support by the operator's teeth. As shown in FIG. 1, housing 2 has generally flat sides 21 and 21A which are joined by top 22 and bottom 23. A housing back 24 is not visible in FIG. 1 but is shown in FIG. 2 as joining the sides, top, and bottom of housing 2.

Variable electrical means such as a straight potentiometer 3 provides a controllably variable resistance signal such as a voltage potential to a controlled machine. The voltage potential is varied by linear movement of post 6 along the length of potentiometer 3.

A first dentition grip 7 is rigidly or semi-rigidly attached to housing 2 by first control arm 8. The control arm 8 is shown as including an adjustment slot 11 through which screw or screws 12 pass, adjustably attaching the first control arm 8 to housing top 22.

A second dentition grip 9 is attached to moveable post 6 on potentiometer 3, such that movement of grip 9 relative to grip 7 varies the position of post 6 on the potentiometer to control the voltage potential thereby.

Dentition grip 9 is joined to post 6 by second control arm 10. This grip 9 also may be attached adjustably in a manner comparable to the adjustability provided for the first dentition grip 7.

As shown in FIG. 1, first dentition grip 7 is comprised of a thermoplastic member 13 which is fixedly joined to dentition grip plate 14. Plate 14 is a rigid or semi-rigid metal or plastic member to which first control arm 8 is joined. Alternately, plate 14 and arm 8 may be a unitary member formed from a single piece of metal or plastic.

Likewise, second dentition grip 9 is comprised of a thermoplastic member 15 which is fixedly joined to dentition grip plate 16. Plate 16 may be formed in a similar fashion to plate 14.

Thermoplastic members 13 and 15 are shaped to contact the upper and lower teeth, respectively, and to be conformed to the shape thereof. For example, members 13 and 15 may be made to fit the tooth patterns 17 and 18 by a dentist. Bite impressions may be made in a heated wax block which is subsequently shaped, invested, and removed from the investments. Thermoplastic members 13 and 15 can then be cast in the investments.

Alternatively, thermoplastic members 13 and 15 may be formed in vivo at a temperature somewhat elevated above body temperature, i.e. greater than 98.6° F. The temperature must not be so high as to burn the operator's mouth. Preferably, the thermoplastic is softenable at a temperature between 115° F. and 220° F. For example, a polymer formed of a mixture of acrylonitrile, butadiene and styrene monomers in proper ratios or blend to achieve such desired softening characteristics may be used. Such blends are known in the art. Dentition plastic members formed out of such polymeric materials are readily softenable by placing them in boiling water, and they remain soft as they cool below their initial softening temperature on heating. Thus they remain soft after withdrawal from boiling water and sufficient cooling to be at a temperature cool enough not to give significant discomfort as one bites into them. On further cooling they revert to a solid state and remain solid at body temperature. While solid they are not unyieldingly rigid and thus are comfortable to fit on and off teeth. It is emphasized that the operator clamps his or her teeth into the heated and softened thermoplastic member or members, and the thermoplastic squeezes around the teeth to surround, embrace, and cling to their exterior surfaces. When the thermoplastic is cooled to body temperature, it remains somewhat flexible but is sufficiently rigid to prevent inadvertent loosening from the teeth. The cooling process may be speeded up by flushing the mouth with cold water while gripping the thermoplastic member. During the conformable process, dentition grip plates 14 and 16 provide a rigid backing for the softened thermoplastic members 13 and 15.

Although the thermoplastic members cling to the teeth during operation of the control unit, they may be easily removed from the teeth by finger manipulation of the formed members away from the teeth. During operation of this invention, of course, there is relatively little force exerted on the thermoplastic members to pull them from the teeth because the control unit is light in weight, and little force is required by the operator to adjust the potentiometer setting or to actuate the switches.

A great advantage of this invention is the freedom of head movement available to the operator. This freedom enhances the speed and accuracy of operation. In the operation of a powered wheelchair, for example, safety also is enhanced by the operator's head mobility.

Second control arm 10 may be attached to post 6 on potentiometer 3 in alternative ways. For example, post 6 may be cemented to control arm 10, or be joined by a screw.

Microswitches 4 and 5 are very lightweight. They are readily obtainable in the trade, and are made by several manufacturers in different electrical configurations, including momentary contact switches. Several styles of detent members are readily available as well. Microswitch conductor means enables various modes of switching to occur to the machine for control thereof, for example by multiwire cable 20.

In FIG. 1, screws 19B are shown as passing through spacers 25 on either side of microswitch 5 and through screw holes 39 in the microswitch, to hold it securely in the proper position, preferably at one end of the potentiometer. Alternately, the switch may be press-fit into position, or held in place by friction. Microswitch 5 may also be cemented to housing 2 or potentiometer 3 in the proper alignment with the potentiometer. If a microswitch 5 is used which has male plug-in terminals, pressing such terminals into receiving sockets mounted in housing 2 may be used as a means of mounting the microswitch.

Microswitch 5, when actuated, signals the controlled machine to start or stop the mechanical or electrical function whose speed or intensity is controlled by potentiometer 3. Typical of such functions are motor speed, sound volume, brightness, and the like.

Microswitch 4 is mounted adjacent the upper portion of potentiometer 3 and has elongated detent member 27 which extends into the vicinity of the operator's tongue. The microswitch may be operated by merely moving detent member 27 slightly upward and/or inward with the tip of one's tongue. The microswitch may alternately be mounted for downward, rather than upward movement of detent member 27.

Microswitch 4 may be mounted in housing 2 by screws 19 or any other means which will hold it securely in place. It may for example be cemented to the side of potentiometer 3.

In FIG. 1, potentiometer 3 is shown separated from, and attached to, housing sidewall 21A by spacers 25A, to which potentiometer 3 and sidewall 21A are cemented. Alternatively, a potentiometer 3 may be used which has male plug-in terminals which fit tightly into a socket. The socket may be secured to housing 2 to hold potentiometer 3 in place within the housing. Potentiometer 3 and the microswitches may be mounted in housing 2 by any means which holds them in proper placement for actuation by the operator's jaw and tongue movements.

Turning now to FIG. 2, a side view of the control unit portion of the invention taken along line 2—2 is shown. The side 21A, top 22, bottom 23, and back 24 of housing 2 are shown. First control arm 8 is shown as slideably mounted on housing top 22 by adjustment screws 12, so that it may be adjusted to comfortably place microswitch detent member 27 within actuation distance of the operator's tongue. Microswitch 4 has two spaced mounting holes 39 therethrough, in accordance with industry standards. These holes are used for accurately mounting the microswitch in housing 2. Screws 19 pass through holes 39 and the housing side 21 to maintain the microswitch in proper orientation.

Microswitch 4 is shown as a single pole, double throw (SPDT) switch having one normally open (NO) terminal 34, one normally closed (NC) terminal 32, and ground terminal 33. Actuation of the microswitch opens the NC terminal and closes the NO terminal. A single pole, single throw (SPST) switch or momentary contact switch, or other type of microswitch may also be used, depending upon the type of switching signal desired.

Potentiometer 3 is vertically mounted in housing 2 to correspond to vertical jaw movement. Second control arm 10 is mounted on potentiometer post 6 and serves to move the post upward or downward in potentiometer 3 by jaw movement.

An electrical potential, for example 5 volts DC, is introduced across the potentiometer through terminals 29 and 31. A moveable contact mounted on post 6 is moved thereby to produce an intermediate potential which is transmitted to terminal 30.

Microswitch 5 is shown as an SPDT switch mounted in housing 2 below potentiometer 3 and spaced from it. Detent member 28 on the upper portion of switch 5 projects outwardly therefrom so that downward movement of extension 10A of second control arm 10 actuates microswitch 5 to close NO terminal 35 and open NC terminal 36. Terminal 37 is normally grounded as indicated.

Any microswitch which is electrically suitable to provide the desired control signal may be used. Standard microswitches have two mounting holes 39 and 39A. Screws 19 and 19B may be passed through the mounting holes to accurately mount the microswitches to housing 2.

FIG. 3 shows the various electrical components and the terminals thereof, as already described. A voltage potential is impressed across potentiometer terminals 29 and 31. Moveable contact 6A is continuously in contact with terminal 30. The controlled voltage between terminals 30 and 31, or alternately between terminals 30 and 29, may be used to control the speed or intensity function of the controlled machine. Either or both of terminals 35 and 36 control ON-OFF functions related to the speed or intensity control function Tongue-actuated microswitch 4 is shown as activating only one circuit through conductors 33 and 34.

For the purposes of this description, each of the terminals of this invention includes the conductor means such as wires to carry the electronic or electrical signal to the machine for control of its functions. Typically, the signals are transmitted through multi-wire cable 20 to control unit 40, which is part of the controlled machine and converts the signals into commands for controlling the machine functions.

FIGS. 4-6 are different views of a straight potentiometer 3 applicable to this invention. A potentiometer case is comprised of two halves 41 and 41A which are connected by screws, rivets, or other connecting means 42. The case is formed of an electrically insulating material, for example, plastic. Post 6 slides in slot 26 and is attached to second control arm 10 which actuates the movement. Terminals 29, 30 and 31 are shown as plug-in members, each adapted to fit into a socket.

FIG. 5 is a front cross-sectional view of potentiometer 3 along line 5—5 of of FIG. 4. Case sides 41 and 41A contain straight resistance member 38, straight metal collector strip 43 connected to terminal 30, and a flexible metal coil 44, the latter being in moveable contact with both resistance member 38 and strip 43. Metal coil 44 is mounted on inner portion 46 of post 6.

FIG. 6 is a side cross-sectional view of potentiometer 3 along line 6—6 of FIG. 4, and shows conductive member 38 mounted in case side 41A. In this example, the conductive member is an elongated flat member of uniform resistance per unit length. Terminals 29 and 31 are connected at opposite ends of conductive member 38 for impressing a known low voltage therebetween.

Flexible metal coil 44 is mounted on the inner portion 46 of post 6 and held thereon by spring retainer portion 47 and slide portion 45. As post 6 and coil 44 are moved along the conductive member 38, the voltage drop between conductors 30 and 31 varies with the distance of coil 44 from the lower end 48 of the conductive member, according to well-known principles.

Because of the limited jaw movement in humans, the useable length of linear conductive member 38 will generally be no greater than about 10 centimeters (about 4 inches), but can vary depending on arm distances from an operator's jaw. Usually the useable length will not exceed about 5 centimeters (about 2 inches), or even a little less, such as no more than 3 or 4 centimeters (about 1½ inches).

The present invention is particularly useful for controlling a programmable sewing machine which is functionally automatic or semiautomatic. Exemplary of such machines are Singer TM sewing machines which use the Programmable Sewing System. The sewing machine is computerized and is designed to operate in any of a number of modes. First, the machine may be operated in the MANUAL mode. Secondly, in the AUTO LEARN mode, operations conducted manually are memorized for subsequent automatic repetitive operation in the AUTO SEW mode. In the KEY LEARN mode, instructions are keyed into memory, for example by a touch console, for subsequent operation in the AUTO SEW mode.

To use these and other possible modes of operation, the operator uses a foot-operated treadle to initiate or control the functions of the particular mode chosen. A microcomputer enables the controller to select a specific mode of operation in which limited commands can be initiated by use of the treadle. In the Singer system, the treadle actuates a potentiometer and two switches whose signals are directed to, and interface with, the microcomputer.

The foot-operated treadle has three positions of operation: (a) Neutral, (b) Sew, and (c) Trim. Without foot pressures, the treadle resides in the neutral position. Forward pressure on the top of the treadle initiates the Sew operation by actuation of a first switch. The sewing speed is increased by increasing forward pressure on the treadle, which operates the potentiometer to provide an increasing voltage potential. A Trim operation whereby the presser foot is raised and the thread trimmed and wiped is initiated by establishing a neutral treadle position followed by heeling of the treadle to actuate a second switch. The trimming operation, also known as heeling, completes and terminates a programmed cycle when the machine is in AUTO SEW mode.

In the AUTO SEW mode, merely depressing the treadle initiates the complete sewing and trimming operation in a previously memorized programmed cycle. In this mode, the pressure on the treadle does not affect the sewing speed, which instead follows the program in memory. The treadle, however, must be maintained in a depressed state until the sewing-trimming cycle is completed. Return to a neutral position halts the machine's operation. Each subsequent cycle is initiated by pressure on the treadle from the neutral position.

In the present invention, the treadle-operated potentiometer is replaced by mouth-operated potentiometer 3 which provides a controllable voltage potential to perform the same function.

Microswitches 4 and 5 perform the same function as the second and first treadle-operated switches, respectively, of the Singer sewing machine. Microswitch 5 establishes a neutral position through conductors 36 and 37 when the operator's jaws are opened to move dentition grips 7 and 9 to their most separated position. When dentition grip 9 is moved upwards (as the operator's jaws are moved toward a closed position), it actuates microswitch 5 to turn on the Sew function of the machine.

Tongue-actuated microswitch 4 performs the same function as the heeling switch of the Singer machine. It is to be operated when microswitch 5 is in the neutral position; that is, the dentition grips are in their most separated position. Microswitch 4, like the foot-operated trim switch it replaces, serves to signal the microcomputer to raise the presser foot and needle, and to trim and wipe the thread to complete the sewing cycle.

The Singer sewing machine uses a knee lifter which, when actuated, manually raises the presser foot. However, the same function may be accomplished by hand operation of the touch console, so independent control of the presser foot is unnecessary. However, an additional tongue-actuated microswitch, which like microswitch 4 is mounted on either side of potentiometer 3, may be used to achieve this function if desired.

The Singer system also includes a foot-operated "jog" switch which permits the machine to advance one stitch with each actuation. While this feature is not essential to operation of the sewing machine, it may be accomplished if desired by mounting an additional tongue-actuated microswitch on either side of potentiometer 3. Neither this microswitch nor that which replaces the knee lifter need be near dentition grip 7, because the jaws will be in the fully open position, i.e., the neutral position, when the presser foot is to be raised or the stitching is to be advanced by the jog switch. These microswitches will be located such that they can be readily actuated by the operator's tongue.

In reference to FIGS. 2 and 3, an electrical potential is provided across conductors 29 and 31. Typically, one of the conductors is grounded. Moveable contact member 6A contacts conductive member 38 of potentiometer 3 intermediate the ends thereof to assume a potential or voltage difference across conductors 30 and 31 or across conductors 30 and 29 which is controlled by the position of contact member 6A along the resistance member 38.

As an example, only two of the three conductors 32, 33 and 34 leading from tongue-actuated microswitch 4 are required to control the Trim function. As shown in FIG. 3, conductor 33 is wired to common ground and conductor 34 leads to microcomputer 40 for initiating the Trim operation.

Microswitch 5 is wired to provide two conductors which carry electronic signals to the microcomputer. As shown in FIG. 3, microswitch 5 has two output terminals, one normally open (NO) and one normally closed (NC). Thus, the switch maintains the sewing machine in either the Sew condition or Neutral condition. Depending upon the particular circuitry of the microcomputer system, either a NO or NC switch may initiate the Sew or Neutral condition. In this example, conductor 37 is shown as a ground connection to microswitch 5. The microswitch is shown closed to Neutral control conductor 36, while Sew conductor 35 is open.

Each of conductors 29, 30, 31, 34, 35 and 36 is shown as interfacing with microcomputer 40 to provide electronic signals for controlling the operation of the machine. Additional microswitches may be mounted on either side of potentiometer 3 to provide control of other functions peculiar to the particular sewing system, such as controlling transmission of signals including those which initiate commands. Transmission is through conductors to microcomputer 40. Where it is desired to control the speed or intensity of more than one operation, a microswitch may be used to switch from one function to the other, so that potentiometer 3 will provide a variable signal for control of each function in the alternative. Thus, it is apparent that this invention may be easily adapted to control a wide variety of sewing machine systems, and more generally, a wide variety of electronically controlled machines of all kinds.

A further embodiment of this invention for controlling a wide variety of machines is illustrated in FIGS. 7-13. As depicted in FIGS. 7 and 8, straight potentiometer 3 is mounted in housing 2 for controlling speed, or motion intensity, and microswitch 5 is mounted below the potentiometer for turning the machine function on or off. Second control arm 10 is attached to potentiometer post 6 for varying the voltage potential thereof. Microswitch 5 is mounted so that its detent member 28 is in line with potentiometer slot 26. As control arm 10 is moved downward near its lowermost position on the potentiometer, its extension 10A overrides detent member 28 and depresses it inward to actuate the switch.

A plurality of tongue-actuated microswitches 49 are mounted on either side or both sides of potentiometer 3. Each has a detent member 50 which when motivated inward by the operator's tongue, actuates the switch. Removeable detent tips 51 are mounted on the outer end of each detent member 50 for ease of actuation. Tips 51 are removed for cleaning and/or sterilization, or replacement, thus ensuring sanitary use by the controller or operator. The detent tips may be made of rubber, plastic, or other material with a slot or other opening into which the ends of the detent member may be inserted.

Detent members 50 are of sufficient length to extend into the easy reach of the operator's tongue but outside the bite of the dentition grips 7 and 9. Spacing of the detent members from each other enables proper discrimination by the operator's tongue to actuate the desired microswitches.

Control signals from potentiometer 3 and the microswitches 5 and 49 are directed by conductor means 20, typically a multi-wire cable, to the machine or control unit being controlled. Alternatively, a micro-transmitter device may be mounted in the housing 2 to transmit vai radio signal the control signals to a receiver on the machine.

In FIG. 8, housing 2 is shown as having a front 52, sides 21 and 21A, top 22 and bottom 23. A backplate 53 covers the rear opening of the housing to enclose the wiring connections therein. Screw holes 54 in housing 2 are aligned with mounting holes 39 and 39A of standard microswitches such that the microswitches may be held in place by passage of screw members 19, 19A and 19B therethrough.

Alternatively, the microswitches 49 and 5 may be cemented to potentiometer 3 to form a unitary group which fits into housing 2. Potentiometer 3 may include potentiometer conductor means 30, as already shown, which firmly mounts in sockets 69 to hold the potentiometer and attached microswitches in place. Other means of mounting may also be used.

In FIGS. 7 and 8, first control arm 8 is shown in adjustable mounting on the upper portion of housing 2 by screw 12 which passes through slot 11 in the control arm. Other means of adjustably attaching first control arm 8 to housing 2 may also be utilized.

Furthermore, both the first and second dentition grips are preferably detachable from control unit 2A to ease their removal from the operator's mouth and to enable their separate cleaning and/or disinfection and/or replacement. One such detachable means is illustrated in FIGS. 9 and 10. First control arm 55 contains a slot 58 for adjustable attachment to housing 2 by fastening means such as screw 12. A bolt and wing nut may be used. One end of arm 55 includes an enlarged section 56 with a slot 57. A tab 59 rigidly attached to one of the two essentially identical dentition grips 60 is inserted into slot 57 and is held therein by friction or other means.

Likewise, second control arm 61 includes an enlarged section 62 with a slot 63 into which tab 59 may be inserted.

As previously described, the dentition grips include thermoplastic members 64 mounted on plates 65.

It will be understood that while this invention is described as having the first dentition grip conformed to the operator's upper teeth and the second dentition grip conformed to the lower teeth, the opposite arrangement may be used.

Housing 2 may take any appropriate form or shape to house potentiometer 3 and microswitches 5 and 50. FIG. 11 shows the particular housing embodiment of FIGS. 7 and 8 which is adaptable to mass production from plastic material, for example. Potentiometer 3 and the microswitches are separated from the outer walls and from each other, where suitable, by spacers 66 which maintain the control elements in the desired location. The internal portions 67 of spacers 66 are preferably hollow to minimize the overall weight and consumption of plastic material in their manufacture. Screw holes 54 are provided for attaching the microswitches, and apertures 68 allow connection of conductors such as wires to the switch terminals on the rear of the microswitches. Sockets 69 in the housing structure 70 receive potentiometer conductor means 30 shown in FIGS. 4–6 and anchor the potentiometer within housing 2.

FIG. 12 is a cross-sectional view of exemplary housing 2, as taken along line 12—12 of FIG. 11. Potentiometer 3 is fitted between spacers 66, having conductor means 30 inserted into sockets 69. Screw members 19 pass through screw holes 54 and mounting holes 39 and 39A in microswitches 49, to anchor them in place. Conductor wires, not shown, connected to the microswitches and potentiometer sockets, pass in a multi-wire cable through grommet 71 to the machine which is controlled. In this embodiment, backplate 53 is attached to the housing 2 by screw 72 passing through matching posts 73 and 74, and seals the rear of the housing.

FIG. 13 shows exemplary control circuits using the oral machine controller of FIGS. 7 and 8. The potentiometer circuit having conductors 29, 30 and 31 is as previously described.

Four tongue-controlled microswitches 49 are preferably shown as SPDT switches, each having one NO terminal and one NC terminal for the sake of example. The pole of each switch is shown as being grounded. Conductors 75 through 82 provide tongue-actuated electronic signals to microcomputer 40 or other signal converter to control the particular machine.

Microswitch 5 is connected through conductors 35 and 36 to microcomputer 40 as previously described.

Thus, numerous functions of a machine may be controlled through the combination of a jaw-actuated potentiometer and microswitch, together with one or more tongue-actuated microswitches.

An operator may use a single oral machine controller of this invention to control a variety of machines, merely by adapting the signal output of this controller to fit the requirements of the machines and using standard interchangeable multiconductor connectors well known in the art. Each machine will then use only the particular conductors required for its operation.

The potentiometer and microswitches of this invention may be easily replaced and are readily available from many commercial sources at low cost.

The voltages used in this invention are relatively low and enable safe operation by persons, whether handicapped or not.

In summary, this invention enables control of various switching functions, cursor control and speed and/or intensity functions of machines by movement of jaw and tongue. Machines otherwise not operable by disabled persons become readily operated by such persons.

While this description illustrates the invention as applied specifically to a programmable sewing machine, it may be used with any machine or machines which may be controlled by electronic or electrical signals.

Although particular embodiments of the invention have been illustrated in the accompanying drawings and described in the foregoing description, it shall be understood that the invention is not limited only to the embodiments and examples disclosed, but also embraces any alternatives, equivalents, modifications and/or rearrangements of elements which are within the scope of the invention as defined by the following claims:

That which is claimed is:

1. An oral control device for electrical control of the operations of a machine by a human operator, comprising:
   (a) a housing;
   (b) a variable electrical resistive means carried by said housing and constructed and arranged to be connected to such a machine in voltage-potential controlling relation;
   (c) said means including a movable control member movable relative to the remainder of said means and constructed and arranged to vary the voltage-potential of said means as said member is so moved;
   (d) a first dentition grip constructed and arranged to be removably attached to the teeth of one jaw of such an operator and connected to said housing in supporting relation; and
   (e) a second dentition grip constructed and arranged to be romovably attached to the teeth of the other jaw of such operator, and connected to said control member in movement controlling relation relative to the remainder of said means, whereby opening and closing jaw movements of such operator will move said control member relative to the remainder of said means and thereby controllably vary the voltage-potential of said means.

2. The structure defined in claim 1, and
(f) switch means carried by said housing and constructed and arranged to be electrically connected to such a machine in controlling relation; and
(g) a plurality of tongue-actuated detent members connected to said switch means in switch-actuating relation.

3. The structure defined in claim 2, and
(h) second switch means carried by one and actuated by the other of said dentition grips by movement of one of said grips relative to the other with the jaws of the operator;
(i) said second switch means being constructed and arranged to be connected in electrically controlling relation with such a machine whereby operation of the machine may be controlled by the operator by movement of one of his jaws.

4. The oral control device according to claim 1, wherein;
said first dentition grip is constructed and arranged for attachment to the teeth of the upper jaw of said operator, and said second dentition grip is constructed and arranged for attachment to the teeth of the lower jaw of said operator.

5. The oral control device according to claim 1 and: means for adjustable attachment of said first dentition grip to said control member.

6. The oral control device according to claim 1 and: tongue actuated switch means mounted in said housing and one or more electrical circuits controlled by said switch means for switching operations of said machine.

7. The oral control device according to claim 6, wherein:
said switch means includes a detent member extending outwardly therefrom.

8. The oral control device according to claim 1, and: jaw-actuated switch means constructed and arranged to be actuated by movement of said second dentition grip.

9. The oral control device according to claim 1, wherein:
said resistive means comprises a resistive potentiometer.

10. An oral control device for electronically controlling the speed and switching functions of a programmable sewing machine by a human operator, comprising:
a control unit comprising:
a housing;
a potentiometer mounted in said housing and having an electrical resistance member with electrical conductor terminals attached at opposite ends thereof and a movable contract member in contact with said resistance member and movable relative thereto to establish a first electrical circuit therethrough with controllably variable voltage for controlling the speed of said sewing machine;
a START microswitch mounted in said housing for turning said sewing machine ON and OFF, and actuated in concert with said potentiometer;
a TRIM microswitch mounted in said housing and having terminals connected in a TRIM circuit for initializing the trimming operation of said sewing machine, said TRIM microswitch being provided with a detent member projecting into the proximity of the tongue of said operator for actuation thereby;
a first dentition grip for removable attachment to the teeth of one jaw of said operator, said first dentition grip being attached to said control unit in supporting relation;
a second dentition grip for removable attachment to the teeth of the other jaw of said operator, and attached to said movable contact member in moving relation relative to said resistance member, whereby closing said jaws from an open position actuates said START microswitch to turn on said sewing machine and increases said variable voltage in said first circuit to increase said sewing speed, and whereby opening said jaws from a closed position reduces said variable voltage in said first circuit to reduce said sewing speed and finally deactivate said START microswitch to turn off said sewing machine; and conductor means for transferring electrical signals from said potentiometer and said microswitches to said programmable sewing machine for control thereof.

11. The oral control device according to claim 10, wherein:
said first and second dentition grips are comprised of thermoplastic members mounted on a backing plate, said thermoplastic members having a softening temperature greater than body temperature and adapted from conformation to said operator's teeth, to embrace and cling thereto.

12. The oral control device according to claim 11, wherein:
said thermoplastic member is constructed and arranged for in vivo conformation to said teeth at a softening temperature between 115° F. and 220° F.

13. The oral control device according to claim 11, wherein:
said thermoplastic member comprises a polymer containing acrylonitrile, butadiene and styrene.

14. The oral control device according to claim 10, wherein:
said first dentition grip is constructed and arranged for attachment to the teeth of the upper jaw of said operator, and said second dention grip is constructed and arranged for attachment to the teeth of the lower jaw of said operator.

15. The oral control device according to claim 10, further comprising:
means for detaching said dentition grips from said control unit and said moveable contact member.

16. The oral control device according to claim 10, wherein:
said START microswitch signals said sewing machine a STOP signal when said first and second dentition grips are furthest apart, and an ON or RUN signal in accordance with a closing movement of said jaws from the openmost position.

17. The oral control device according to claim 10, further comprising:
one or more additional tongue-actuated microswitches mounted in said housing for control of switching functions of said sewing machine, said additional microswitches having detent members projecting into the proximity of the tongue of said operator for actuation thereby and conductor means for initiating command signals from said additional microswitches to said sewing machine for control thereof.

18. The oral control device according to claim 10, wherein:

said oral control device is constructed and arranged to be completely supported by said teeth of said operator, allowing freedom of movement of said operator's head without affecting the operation of said device by the operator.

19. An oral control device for electrical control of the operations of a machine by a human operator, comprising:

(a) a first dentition grip member constructed and arranged to be removably attached to the teeth of one jaw of such an operator;
(b) a second dentition grip member constructed and arranged to be removably attached to the teeth of the other jaw of such operator;
(c) switch means carried solely by one of said dentition members and constructed and arranged to be actuated by movement of the other of said members relative thereto with the jaws of such an operator;
(d) said switch means being constructed and arranged to be connected in electrically controlling relation to such a machine whereby operation of the machine may be controlled by the operator by movement of one of his jaws.

* * * * *

UNITED STATES PATENT AND TRADEMARK OFFICE
CERTIFICATE OF CORRECTION

PATENT NO.   :  4,728,812

DATED        :  March 1, 1988

INVENTOR(S)  :  Paul S. Sheriff et al

It is certified that error appears in the above-identified patent and that said Letters Patent is hereby corrected as shown below:

Column 8, lines 29-30, "or motion intensity" should read
--intensity, or motion--.

Claim 1, subparagraph (e), Line 2, change "romovably" to --removably--.

Signed and Sealed this

Fifth Day of December, 1989

Attest:

JEFFREY M. SAMUELS

Attesting Officer     Acting Commissioner of Patents and Trademarks